(12) United States Patent
Choi et al.

(10) Patent No.: US 12,421,244 B2
(45) Date of Patent: Sep. 23, 2025

(54) PHTHALOCYANINE NANOWIRES AND USES THEREFOR

(71) Applicant: POSTECH RESEARCH AND BUSINESS DEVELOPMENT FOUNDATION, Pohang-si (KR)

(72) Inventors: Hee Cheul Choi, Pohang-si (KR); Young Kwan Yoon, Pohang-si (KR)

(73) Assignee: POSTECH RESEARCH AND BUSINESS DEVELOPMENT FOUNDATION, Pohang-Si (KR)

( * ) Notice: Subject to any disclaimer, the term of this patent is extended or adjusted under 35 U.S.C. 154(b) by 697 days.

(21) Appl. No.: 17/778,510

(22) PCT Filed: Jul. 30, 2020

(86) PCT No.: PCT/KR2020/010060
§ 371 (c)(1),
(2) Date: May 20, 2022

(87) PCT Pub. No.: WO2021/101016
PCT Pub. Date: May 27, 2021

(65) Prior Publication Data
US 2023/0019169 A1 Jan. 19, 2023

(30) Foreign Application Priority Data
Nov. 20, 2019 (KR) .......... 10-2019-0149244

(51) Int. Cl.
*C07D 487/22* (2006.01)
*B82Y 30/00* (2011.01)
*B82Y 40/00* (2011.01)
*C30B 29/60* (2006.01)

(52) U.S. Cl.
CPC ............ *C07D 487/22* (2013.01); *B82Y 30/00* (2013.01); *B82Y 40/00* (2013.01); *C30B 29/60* (2013.01); *C07B 2200/13* (2013.01)

(58) Field of Classification Search
CPC .................................................. C07D 487/22
See application file for complete search history.

(56) References Cited

U.S. PATENT DOCUMENTS 9,415,106 B2 8/2016 Choi et al.

FOREIGN PATENT DOCUMENTS

| | | |
|---|---|---|
| CN | 1952223 | 4/2007 |
| CN | 102206863 | 7/2012 |
| CN | 103322800 | 9/2013 |
| CN | 104557962 | 4/2015 |
| JP | 3928066 | 6/2007 |
| JP | 2014-534953 | 12/2014 |
| KR | 10-2011-0134478 | 12/2011 |
| KR | 10-1195078 | 10/2012 |
| KR | 10-1352931 | 1/2014 |
| KR | 10-1361755 | 2/2014 |
| KR | 10-2017-0097030 | 8/2017 |
| WO | 2003-076332 | 9/2003 |
| WO | 2010/122921 | 10/2010 |

OTHER PUBLICATIONS

Hye Kyung Moon et al., "Significant increase in the water dispersibility of zinc phthalocyanine nanowires and applications in cancer phototherapy", NPG Asia Materials (2012) 4, e12; doi:10.1038/am.2012.22.

Dongjea Seo et al., "Structural modulation of silicon nanowires by combining a high gas flow rate with metal catalysts", Nanoscale Research Letters (2015) 10:190, DOI 10.1186/s11671-015-0893-4.

Andreas Menzel et al., "Role of Carrier Gas Flow and Species Diffusion in Nanowire Growth from Thermal CVD", J. Phys. Chem. C 2012, 116, 5524-5530, Feb. 1, 2012.

Andreas Menzel et al., "Role of Carrier Gas Flow and Species Diffusion in Nanowire Growth from Thermal CVD", The Journal of Physical Chemistry C 116.9 (2012): 5524-5530, DOI: 10.1021/jp212635w, Feb. 1, 2012.

*Primary Examiner* — Paul V Ward
(74) *Attorney, Agent, or Firm* — LEX IP MEISTER, PLLC

(57) ABSTRACT

M-phthalocyanine nanowires according to the present invention can have a variety of uses as the M-phthalocyanine nanowires can control the crystalline structure thereof by controlling the flow speed of a carrier gas to a suitable range, and can exist in hydrophilic solvent without agglutinating due to superb dispersibility in waterphase.

8 Claims, 9 Drawing Sheets

PHTHALOCYANINE NANOWIRES AND USES THEREFOR

TECHNICAL FIELD

The present invention relates to novel phthalocyanine nanowires and uses therefor.

BACKGROUND ART

Controlling the crystal structure of organic and inorganic crystals is an important requirement for systematic studies of polymorphic crystals. Among various crystal growth methods, the PVT (Physical Vapor Transport) method widely used to grow numerous organic and inorganic crystals of various dimensions, including ZnPc NWs has been considered challenging for growing crystals of a selective structure. This difficulty arises because the crystal structure is typically fixed by intrinsic thermodynamic properties, and the PVT method operates at a fixed temperature with various dynamic parameters.

It is very common for organic and organometallic molecular crystals to have one or more polymorphs due to diverse, weak, and non-directional intermolecular van der Waals forces. In particular, the polymorphisms of several phthalocyanines with various weak interaction sites have been widely studied because their electrical and optical properties differ depending on their laminated structures. For example, $\alpha$-phase titanyl phthalocyanine exhibits 250-750 times higher mobility than $\beta$-phase titanyl phthalocyanine, due to interlayer electron coupling. In addition, the different $\pi$-$\pi$ laminated interactions of triclinic and monoclinic lead phthalocyanine exhibit different Q-band absorption properties, indicating that the electronic structure of lead phthalocyanine may be easily controlled by changes in the laminated structure.

Among the various phthalocyanines with polymorphic structures, the target molecule ZnPc has received much attention as a promising photosensitizer for cancer phototherapy. ZnPc not only shows a photodynamic effect of destroying malignant tumors by generating cytotoxic reactive oxygen species, but also has a large light absorption cross-section in the tissue-transmission spectral wavelength range of 650-900 nm. However, a critical limitation to the practical application of ZnPc is its high hydrophobicity, which leads to poor solubility in bodily fluids. Various approaches have been developed to address this limitation, such as ZnPc derivatives with improved water solubility and transporters to enable ZnPc delivery. However, these methods often require complex post-processing, which can produce various by-products and lead to unavoidable damage.

Previously, the present inventor reported high-quality $\alpha$-form ZnPc nanowires (NWs) with improved water dispersibility and dual photodynamic and photothermal efficiency, all of which had synergistic effects in cancer phototherapy in vitro and in vivo. However, the difficulty in separating the $\alpha$- and $\beta$-forms of ZnPc, which are obtained simultaneously, remains a significant limitation for actual anticancer applications, because the presence of even a small amount of $\beta$-form ZnPc causes aggregation and precipitation in solution. Accordingly, achieving high-quality and high-yield $\alpha$-form ZnPc NWs is an important and urgent problem for practical applications, including clinical trials.

In this regard, the present inventor focused on the development of an easy and efficient method for the selective growth of $\alpha$-form ZnPc NWs. In various Pc studies, it is well known that the crystalline phase is closely related to crystal size. However, solution-phase crystallization is difficult to control in terms of crystal size unless additional chemicals such as capping agents or surfactants are used. Therefore, the PVT method, a gas-phase crystallization method suitable for obtaining pure, high-quality crystals, was employed. It was found that the flow speed of the carrier gas was closely related to the size of the crystals formed. By increasing the carrier gas flow speed, it is possible to reduce the crystal size of ZnPc NWs and to grow $\alpha$-form ZnPc NWs at a high yield. In particular, $\beta$-form ZnPc NWs grown at a carrier gas flow speed of 2000 sccm exhibited very high water dispersibility, showing minimal agglomeration after 8 hours of dispersion in water.

In particular, in Korean Patent No. 10-1352931 a related document to the present invention the carrier gas flow speed used to transport vaporized phthalocyanine was merely 800 sccm, and the weight percentage of the $\alpha$-form phthalocyanine produced through this process was approximately 90% by weight. Consequently, a significant amount of $\beta$-form phthalocyanine compound remained, leading to relatively poor water dispersibility.

Recognizing this limitation, the present inventor developed a high-purity, high-yield phthalocyanine compound upon noting that the ZnPc NW of the present invention may be used to understand molecular crystallization particularly for controlling the crystal structure of phthalocyanine and for commercializing actual cancer treatments.

DISCLOSURE

Technical Problem

The present invention is directed to providing a method of preparing M-phthalocyanine nanowires, the method comprising:

1) vaporizing M-phthalocyanine, wherein M is zinc or copper;

2) transporting the vaporized M-phthalocyanine of step 1) using an inert gas at a flow speed of 1900-2100 sccm; and 3) collecting the transported vaporized M-phthalocyanine of step 2) and precipitating the same in the form of M-phthalocyanine crystals.

In addition, the present invention is directed to providing M-phthalocyanine nanowires prepared by the above preparation method.

Technical Solution

One aspect of the present invention provides a method of preparing M-phthalocyanine nanowires, wherein M is zinc or copper. The method comprises:

1) vaporizing M-phthalocyanine, wherein M is zinc or copper;

2) transporting the vaporized M-phthalocyanine of step 1) using an inert gas at a flow speed of 1900-2100 sccm; and 3) collecting the transported vaporized M-phthalocyanine of step 2) and precipitating the same in the form of M-phthalocyanine crystals.

The phthalocyanine of the present invention has the chemical structure of the compound of Formula 1 below.

[Formula 1]

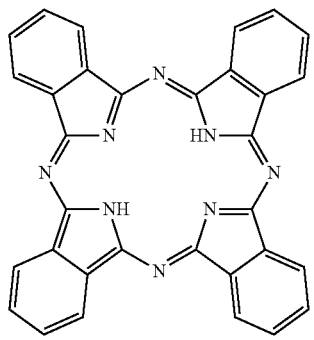

[Formula 3]

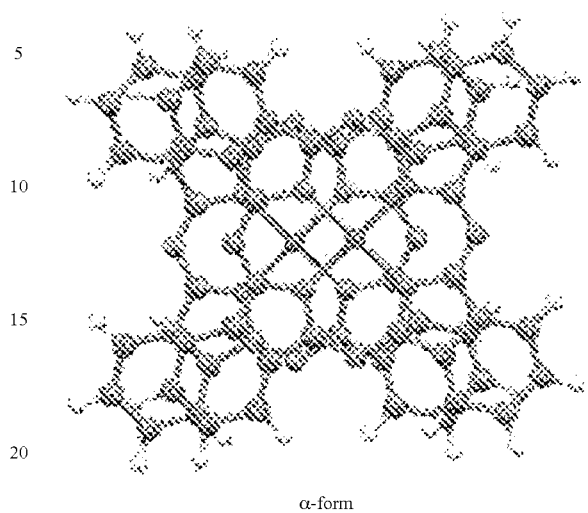

α-form

In a specific embodiment, the M of M-phthalocyanine may be bonded to four nitrogen atoms inside the phthalocyanine ring, as in the compound of Formula 2 below.

[Formula 2]

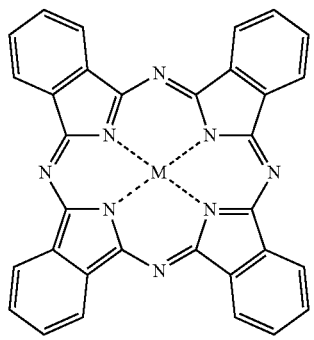

M may be zinc or copper, but is not limited thereto.

In step 2), the weight percentage of α-form M-phthalocyanine crystals may be selectively controlled by adjusting the flow speed of the inert gas. A preferred inert gas may be argon, though any inert gas suitable as a carrier gas for condensing and recrystallizing vaporized M-phthalocyanine may be used.

The flow speed of the inert gas may be in the range of 1900 to 2100 sccm, preferably in the range of 1950 to 2050 sccm, and most preferably in the range of 2000 sccm. By controlling the inert gas flow speed within the above range, the weight of the α-form M-phthalocyanine crystals of the following Formula 3 may be selectively controlled.

The M-phthalocyanine compound of step 1) is characterized in that the alpha (α)-form M-phthalocyanine nanowire according to the present invention is obtained by vapor-condensation-recrystallization (VCR) of M-phthalocyanine. More specifically, the α-form M-phthalocyanine nanowire may be obtained by heating the raw material M-phthalocyanine (e.g., in powder form) to 470 to 700° C., preferably 470 to 600° C., or more preferably 500° C.; then condensing and recrystallizing the evaporated vapor on a substrate at a lower temperature than the heating temperature (e.g. room temperature to 80° C.). During this process, M-phthalocyanine grows in the form of nanowires on the substrate. The diameter of the α-form M-phthalocyanine nanowire may be about 30 to 50 nm, and its length may be about 1 to 10 μm. Collection in step 3) may be performed by condensing and recrystallizing on a Si(100) substrate at room temperature to 80° C.

Unlike conventional phthalocyanine powder, the α-form M-phthalocyanine nanowire displays excellent solubility and dispersibility in water, with remark ably improved stability in aqueous solution (it remains stable for over 3 months). Its aqueous solubility can be further enhanced by agitation, such as sonication. The solubility and dispersibility in water for the obtained α-form M-phthalocyanine nanowires can reach up to 120 mg/L at room temperature.

Another aspect of the present invention provides M-phthalocyanine nanowires prepared by the above method.

The M-phthalocyanine nanowire may include at least 95% by weight of α-form crystals, preferably 98% or more by weight. The crystal form's weight percentage can b e controlled by adjusting the inert gas flow speed to the appropriate range as described above.

The M-phthalocyanine compound is mainly a mixed crystal form of α and β forms, mainly α-form having the crystal structure of Formula 3 above. The α-form crystals are the major phase constituting at least 50% of the crystalline forms. Since the presence of the β-form phthalocyanine causes aggregation and precipitation in solution, it may contain 95% by weight, preferably 98% by weight or more, and most preferably more than 98% by weight of α-form crystals to maintain excellent water dispersibility.

Overlapping contents are omitted in consideration of the complexity of the present specification, and terms not defined otherwise in the present specification have the meanings commonly used in the technical field to which the present invention pertains.

Advantageous Effects

M-phthalocyanine nanowires according to the present invention can be used for various applications. By controlling the flow speed of a carrier gas within a suitable range, one can control the crystal structure. Additionally, these nanowires exhibit excellent dispersibility in water, allowing them to exist in hydrophilic solvents without agglomeration.

MODES OF THE INVENTION

Hereinafter, preferred examples are presented to help the understanding of the present invention. However, the following examples are only provided for easier understanding of the present invention, and the content of the present invention is not limited by the examples.

EXAMPLES

Example 1. Preparation of ZnPc and CuPc Nanowires and Analysis of Changes in Characteristics of Nanowires According to Carrier Gas Flow Speeds By using ZnPc powder as a precursor, alpha (α) type ZnPc nanowires were prepared through the vaporization-condensation-recrystallization (VCR) process, a form of physical vapor transport (PVT).

Figure 1:
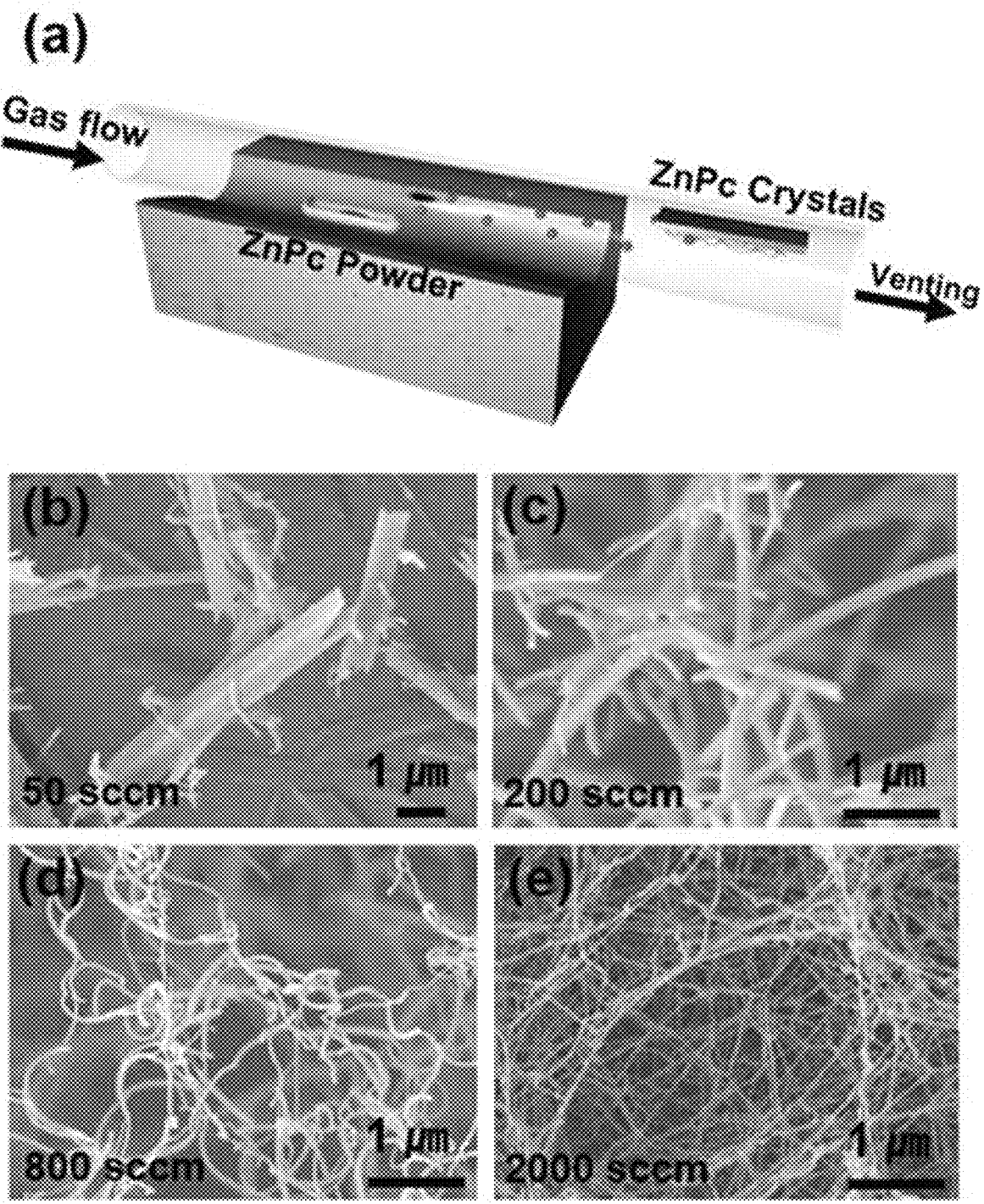
FIG. 1 shows an experimental plan and the morphology of ZnPc crystals grown under different flow speeds. (A) Schematic diagram of the PVT system used to grow ZnPc crystals. (B)-(E) SEM images of ZnPc crystals grown with carrier gas flow speeds of 50, 200, 800, and 2000 sccm, respectively.

ZnPc nanowires and CuPc nanowires were prepared using commercially available zinc phthalocyanine (ZnPc, 97%, Sigma-Aldrich) and copper phthalocyanine (CuPc, 97%, Sigma-Aldrich) precursors, respectively, with no additional purification. Specifically, ZnPc or CuPc powder (0.02 g, Sigma-Aldrich) was loaded into a ceramic boat located at the center of a quartz tube in an electric heating system. Approximately 20 mg of precursor loaded into a ceramic boat was placed in the center of a tube furnace using a quartz protective tube. A piece of Si substrate was placed at the end of the quartz tube, where the temperature was naturally reduced below 80° C. to effectively collect the crystals. After flushing the quartz tube with Ar gas at a flow speed of 1000 sccm for 5 minutes, the furnace temperature was increased up to 500° C. under specific Ar flow speeds (50, 200, 800, and 2000 sccm). After reacting at the target temperature for 10 minutes, the furnace was turned off and allowed to cool naturally to room temperature. This VCR process is schematically shown in FIG. 1(A).

The morphology of the prepared crystals was analyzed by scanning electron microscopy (SEM, JSM-7401F, JEOL). To prevent electronic charging of the crystal, platinum was coated onto the crystal surface to form a conductive layer. X-ray diffraction patterns for ZnPc and CuPc crystals were obtained from the 5D beamline at the Pohang Accelerator Laboratory (PAL). All data were converted to the wavelength of CuKα ($\lambda$=1.541841 Å) for easier comparison with reference patterns. A high-resolution transmission electron microscope (HRTEM, JEM-2200FS, JEOL) was used for structural analysis, and samples for TEM measurements were prepared by stamping the ZnPc crystals onto a carbon-coated Cu grid.

Figure 2:
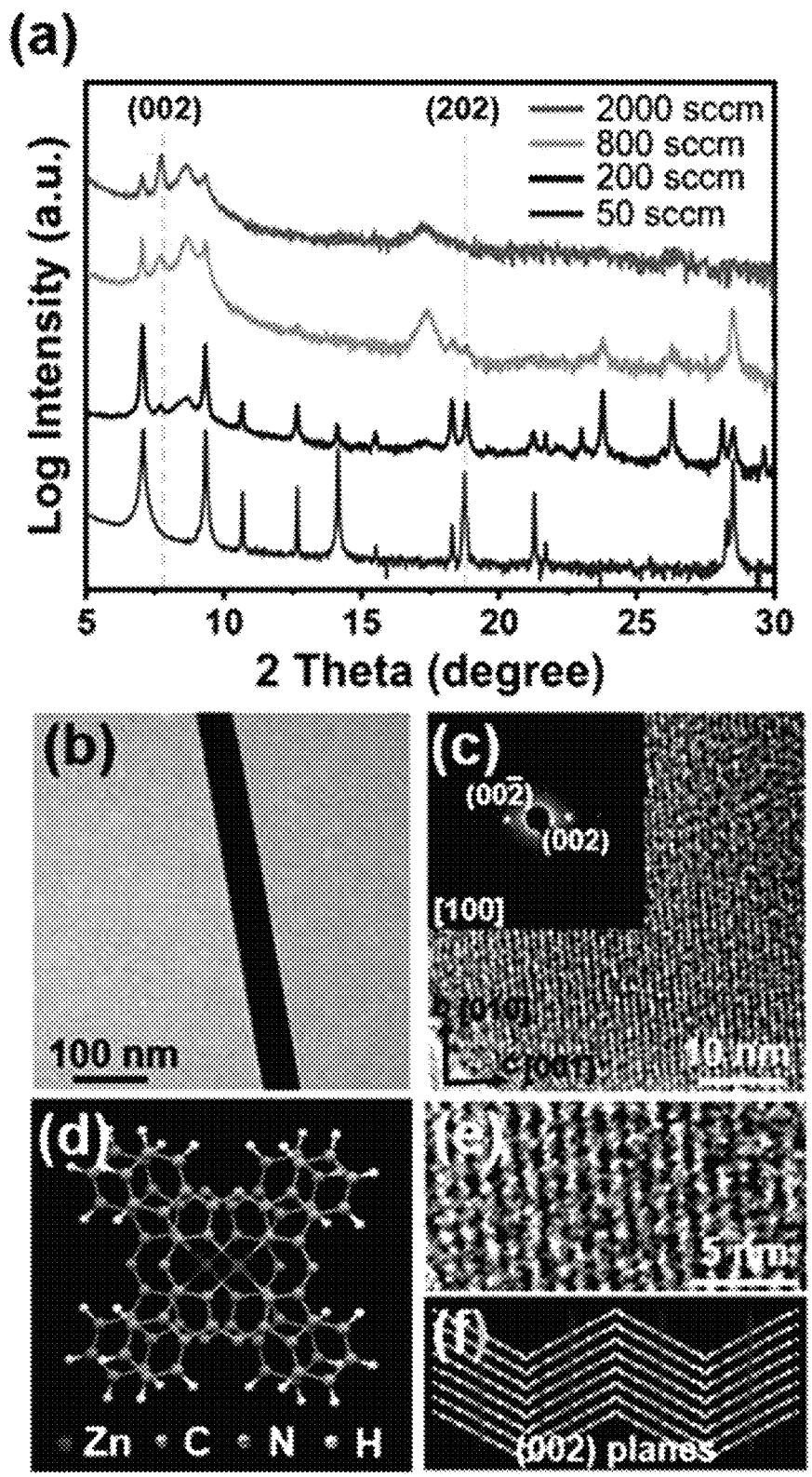
FIG. 2 relates to crystal structure analysis of α-form ZnPc crystals. (A) PXRD patterns of ZnPc crystals grown at different flow speeds, (B) low-magnification TEM image, (C) high-resolution TEM image of α-form ZnPc NWs ([100] SAED pattern of ZnPc NWs by projection), (D) a laminated arrangement of α-form ZnPc crystals along the normal direction of plane molecules, (E) a magnified image of (C), and (F) a schematic diagram of consecutive ZnPc molecular layers for projection.

The stability of α- and β-form ZnPc crystals is affected by crystal size due to their lattice potential and surface energy. According to Buckingham's equation used to estimate the interatomic unbonding potential of organic molecular crystals, α-form ZnPc is more stable than β-form when the crystal size is smaller. In general, in the case of a vapor deposition process, the crystal size is greatly affected by the flow speed of the carrier gas. Accordingly, the flow speed of argon gas was adjusted from 50 to 2000 sccm to selectively obtain α-form ZnPc crystals. FIGS. 1(B) to 1(E) show SEM images of ZnPc crystals obtained in argon gas at different flow speeds. As the flow speed increased, the crystal width decreased from about 460 nm (at 50 sccm (FIG. 1(B)) to 35 nm (at 2000 sccm (FIG. 1(E)). To identify the crystal structure of the ZnPc crystals, powder X-ray diffraction (PXRD) and high-resolution transmission electron microscopy (HR-TEM) were performed. FIG. 2(A) shows PXRD spectra of crystals grown under different flow speed conditions. Due to the different packing structures of α-form and β-form ZnPc crystals, X-ray diffraction patterns with each different characteristic were shown. One of the representative characteristic diffraction planes of the α and β forms of ZnPc crystals are the (002) and (202) planes showing diffraction peaks at 2θ=7.712 and 2θ=18.783, respectively.

In the case of the ZnPc crystal grown at a flow speed of 50 sccm (black line in FIG. 2(A)), the diffraction peak of the (202) plane of the β-form was clearly shown, and the (002) plane of the α-form was absent, which means that the β-form ZnPc crystals are obtained predominantly in the carrier gas at a relatively low flow speed. On the other hand, as the (202) diffraction peak of the β-form gradually decreased and the flow speed increased, the (002) peak observed in the α-form appeared newly. At a flow speed of 2000 sccm (red line in FIG. 2(A)), a clear (002) diffraction plane of α-form and disappearance of a (202) diffraction plane of β-form was observed, which indicates that the α-form ZnPc crystal selectively grows at a relatively high flow speed. These results showed that the crystalline phase of ZnPc may be successfully controlled by changing the flow speed of the carrier gas in the PVT method.

Example 2. Crystal Structure Analysis of ZnPc Crystals

Figure 4:
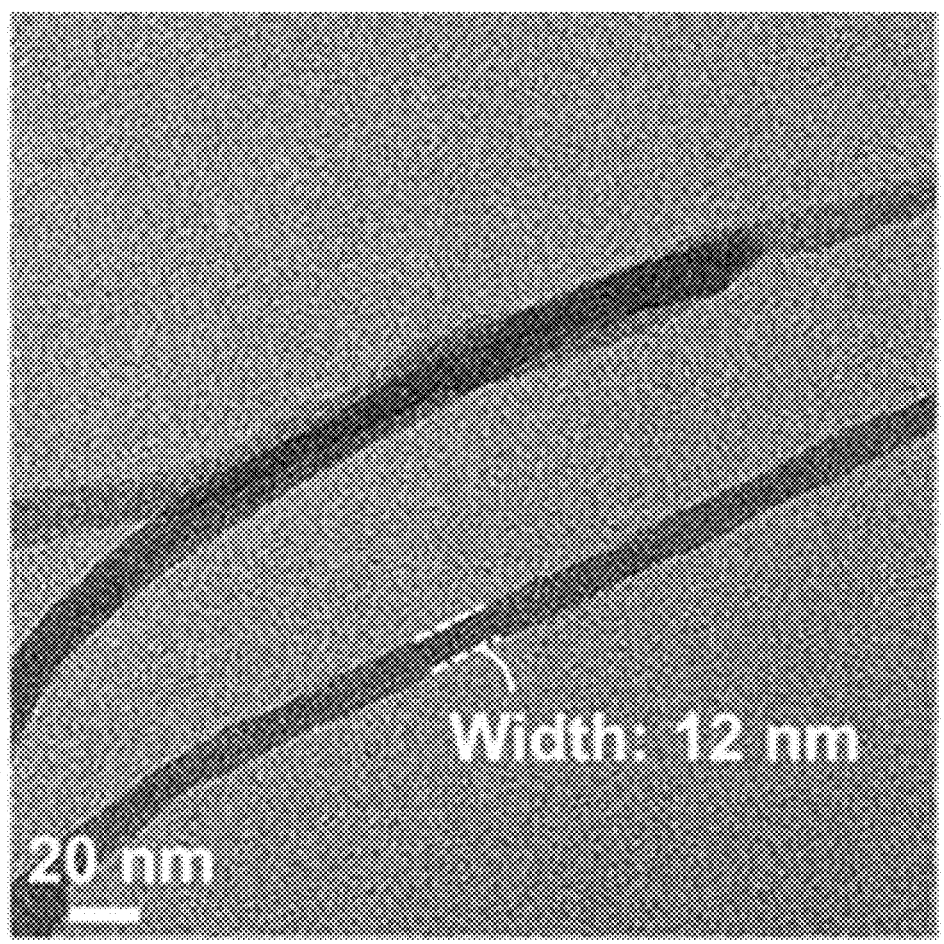
FIG. 4 shows a TEM image of an α-form ZnPc nanowire having the thinnest width (12 nm) obtained at a flow speed of 2000 sccm.
Figure 5:
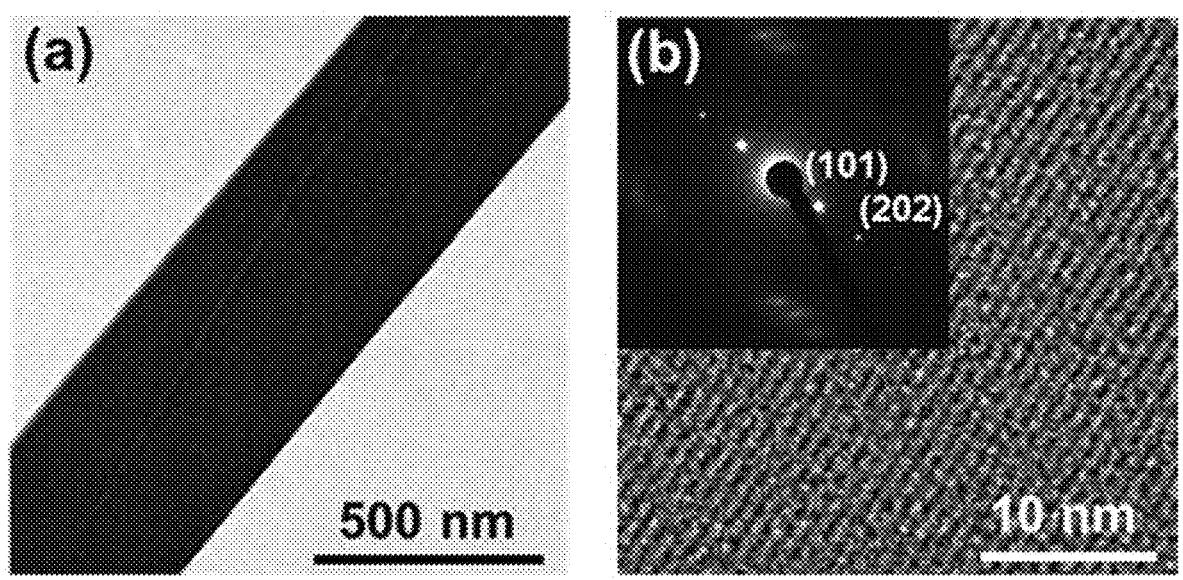
FIG. 5 relates to the crystal structure analysis of the β-form ZnPc nanowires, showing (A) a low-magnification TEM image and (B) a high-magnification TEM image.

The characteristic crystal planes of α-form and β-form ZnPc crystals were also identified through TEM measurements. FIG. 2(B) shows a low-magnification image of α-form ZnPc NWs with uniform surfaces, approximately 50 nm in width and several micrometers in length. The thinnest NW formed at 2000 sccm was about 15 nm wide, specifically 12 nm (FIG. 4). FIGS. 2(C) and 2(E) are HR-TEM images of α-form ZnPc NWs showing well-defined crystal planes. FIG. 2(C) is an electron diffraction pattern of NWs showing a clear diffraction spot with a lattice distance of 1.134 nm which is in good agreement with the distance of the (002) diffraction plane observed in the PXRD pattern of FIG. 2(A) (d(002)-11.464 Å at 2θ=7.712). FIG. 2(E) is an enlarged image of the (002) lattice corresponding to the aligned Zn ions as described by the red line in FIG. 2(F). FIG. 2(D) is the molecular structure and detailed staking arrangement of α-form ZnPc along the b-axis, which shows the growth direction of ZnPc NWs along the stacked direction by π-π interactions. The biggest difference in the molecular packing structure of α and β-form ZnPc is the angle between the column direction (b axis) and the normal direction of the planar ZnPc molecule. Due to the smaller angle ($\approx 25°$ of the α-form than that of the ZnPc β-form ($\approx 45°$, the zinc and nitrogen atoms of the α-form ZnPc NW may use bonding sites that may interact with water molecules by coordination and hydrogen bonding. On the other hand, the water molecule forms a coordination bond between the Zn (II) ion and the ZnPc adjacent to the nitrogen atom. In addition, a well-defined single crystal structure of the β-form ZnPc crystal was identified (FIG. 5). The lattice distance of the (202) plane of the β-form is 0.480 nm, which is in good agreement with the PXRD result of FIG. 2(A) (2θ=18.783 at d(202)=4.724 Å). From the crystal structure analysis of the ZnPc crystals obtained under each flow speed condition, direct evidence was first identified for the relationship between the crystal phase and the carrier gas flow speed, which was the key for the selective growth of α-form ZnPc.

Figure 3:
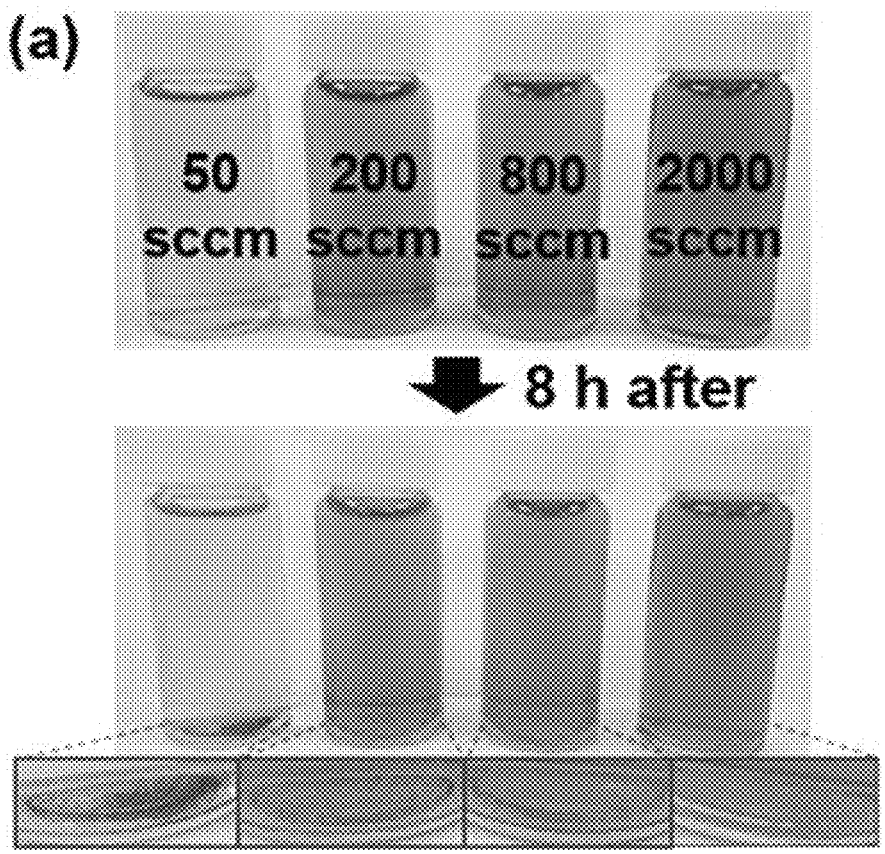
FIG. 3 relates to a statistical study on ZnPc crystals obtained from the water dispersibility test under different flow speeds. (A) images of ZnPc crystals dispersed in water according to carrier gas flow speed, and (B) the statistical widths and α-type wt % trend of ZnPc crystals grown at different flow speeds.
Figure 3:
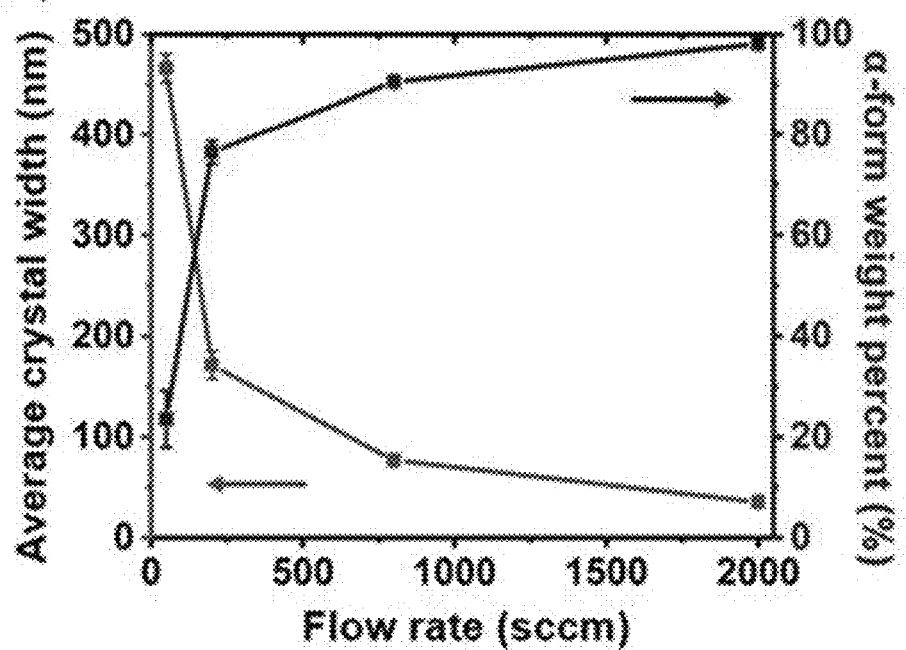

Example 3. Water Dispersibility Test and Statistical Analysis of ZnPc and CuPc Crystals ZnPc and CuPc nanowire dispersion in aqueous solution was prepared by adding crystals collected on a Si substrate to water and then sonicating them in a bath sonicator (UCS-10, JEIOTECH) for 40 minutes. For quantitative analysis of α-form ZnPc crystals obtained at different flow speeds, the unique light absorption band of α-form was measured using a UV-VIS spectrometer (UV-2600, SHIMADZU). In order to obtain reference data indicating the relationship between the concentration and absorbance of the α-form, the α-form ZnPc was isolated from a ZnPc solution stored for 24 hours after dispersing ZnPc in deionized water. A schematic diagram of this experimental procedure is shown in FIG. 7(A). The isolated α-form ZnPc showed a characteristic diffraction pattern of the α-form (FIG. 7(C)), and the UV-VIS spectra of the five reference solutions showed the same peak position and increased absorption intensity as the concentration increased. (FIG. 7(D)) The concentration and absorbance showed a linear relationship as shown in FIG. 3(E).

Based on the reference data, the concentration of α-form ZnPc in each solution obtained at different flow speeds was determined by measuring the light absorbance at 730 nm of the upper (well-dispersed) portion of the ZnPc solution stored for 8 hours. By matching the absorbance of the solution of interest with the reference linear fitting data shown in FIG. 7(E), the concentration of α-form ZnPc was multiplied by the volume of water to calculate the weight % of α-form ZnPc at each flow speed condition.

A major advantage of α-form ZnPc is that the water dispersibility is greatly improved. To identify the water dispersibility of the ZnPc and CuPc crystals obtained under different flow speed conditions, equal amounts of each product were dispersed in deionized water (DI). The upper portion of FIG. 3(A) is a photograph of a solution obtained after 40 minutes of sonication to uniformly disperse ZnPc. Except that the leftmost solution prepared using the ZnPc crystal obtained at a flow speed of 50 sccm had a light blue color, the other solutions showed a similar dark blue color. After storage for 8 hours at ambient conditions, the ZnPc solution prepared by crystals obtained at a flow speed of 50 sccm showed strong precipitation, and the amount of precipitation decreased as the flow speed increased. (Bottom of FIG. 3(A)) In particular, a solution prepared using ZnPc crystals obtained at a flow speed of 2000 sccm (rightmost of FIG. 3(B)) exhibited improved water dispersibility without significant precipitation. These results were in good agreement with the PXRD data in which the proportion of α-form ZnPc increased as the carrier gas flow speed increased.

Figure 6:
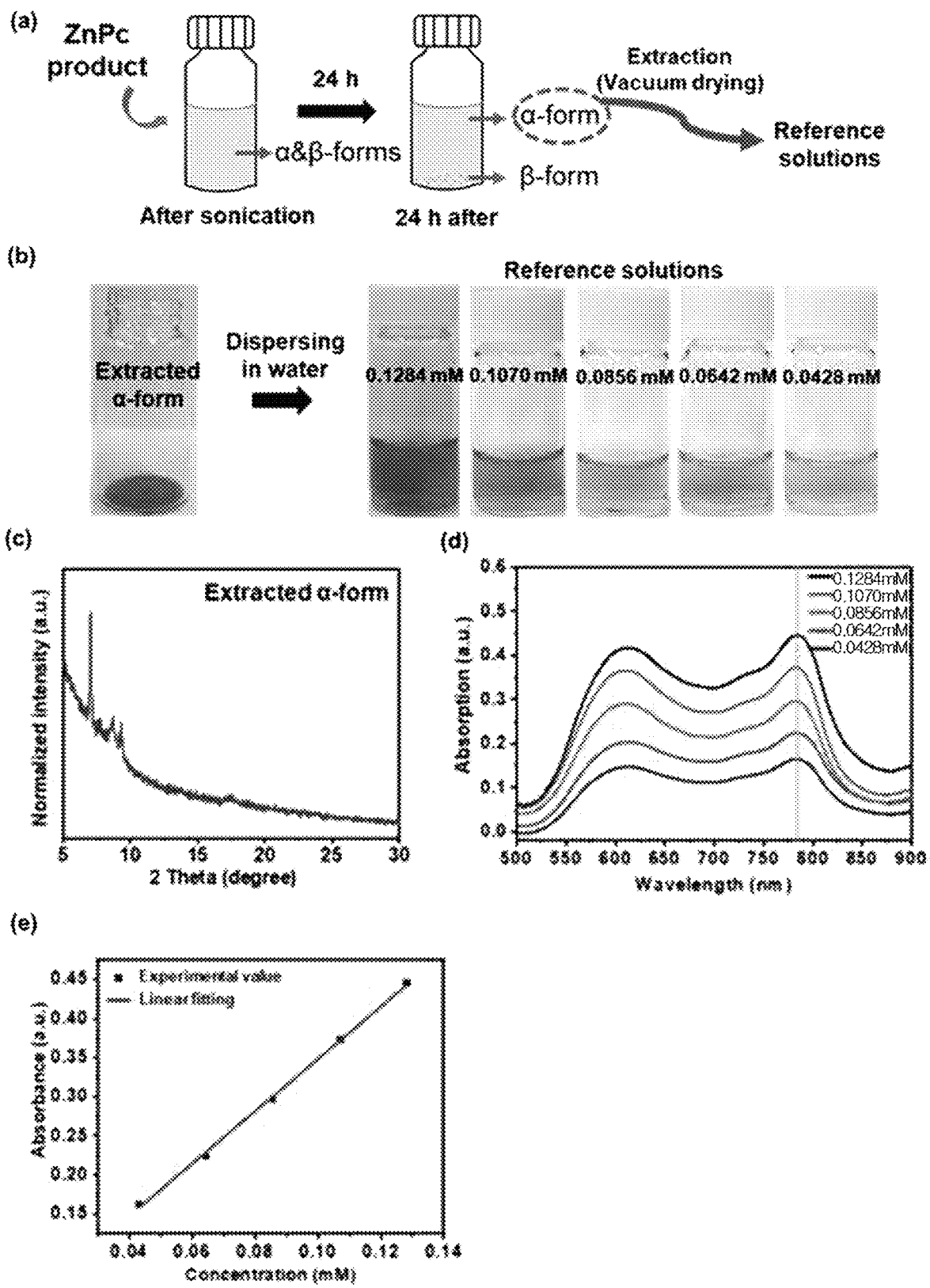
FIG. 6(A) is a schematic diagram for obtaining an α-form ZnPc reference solution, (B) shows images of α-form ZnPc and the reference solution extracted at various concentrations, (C) shows a PXRD pattern of the extracted α-form ZnPc, (D) shows a UV-VIS spectrum of the reference solution, and (E) shows a linear fitting graph between the absorbance and concentration of the α-form ZnPc reference solution.

For quantitative analysis of α-form ZnPc in each solution, the UV-VIS spectrum of the solution remaining after separation of the precipitate (β-form ZnPc) was measured (FIG. 6(D)). Using the characteristic absorption peak of α-form ZnPc at 780 nm, the weight percentage of α-form ZnPc in solution was calculated by comparing the peak intensity with the absorption spectrum of a reference solution. As expected from the PXRD data (FIG. 2(A)), the calculated weight percent of α-form ZnPc in the product increased as the flow speed of the carrier gas increased (blue line in FIG. 3(B)). In addition, surprisingly, at a flow speed of 2000 sccm, the percentage of α-form exceeded 98%. The black line in FIG. 3(B) shows the relationship between the average width and the flow speed of ZnPc crystals that decrease as the flow speed increases from 460 nm (50 sccm) to 35 nm (2000 sccm). By comparing and analyzing the above three important values, average width, percentage and flow speed of carrier gas of α-form ZnPc NWs, it was clearly identified that α-form ZnPc grew significantly favorably in carrier gas with high flow speed, which effectively reduces the width of NWs.

Figure 7:
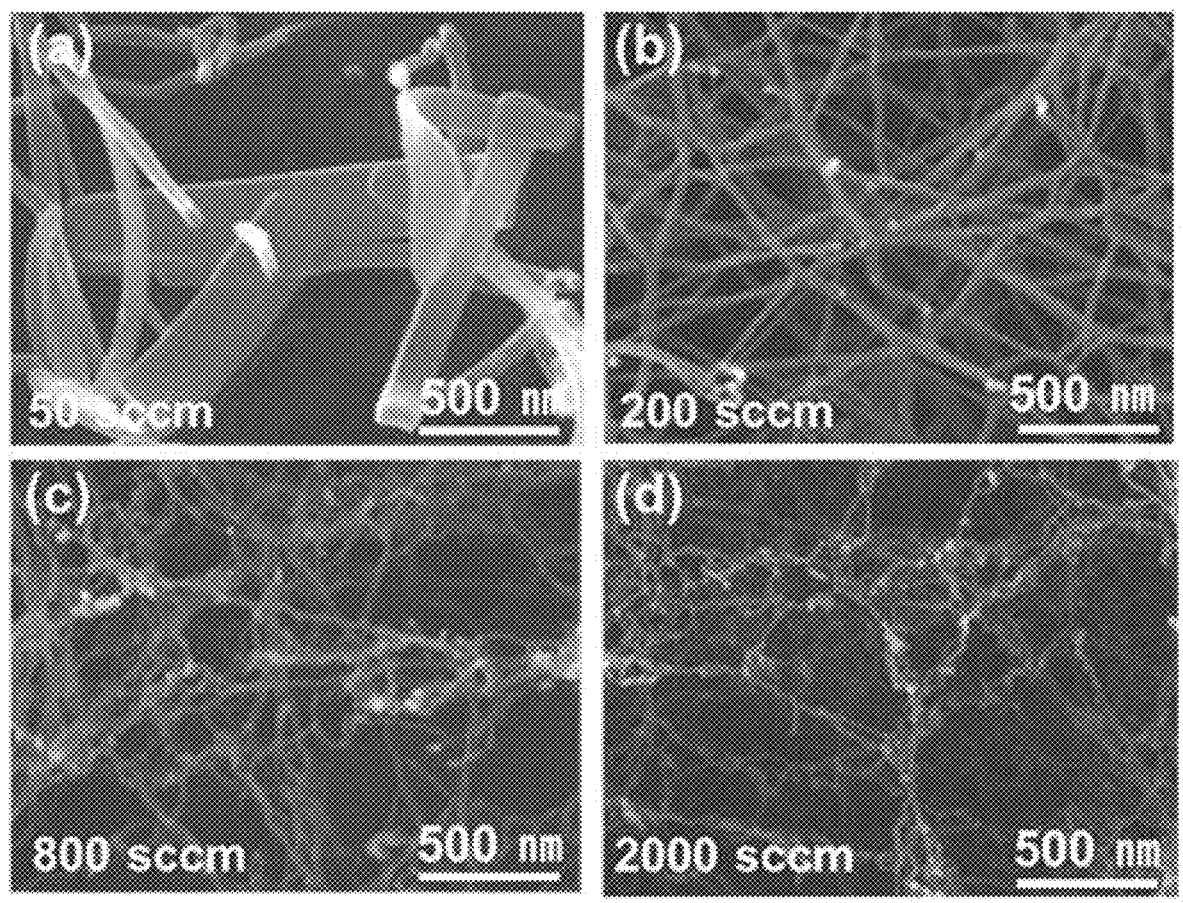
FIG. 7 shows SEM images of CuPc crystals grown at a flow speed of (A) 50 sccm, (B) 200 sccm, (C) 800 sccm, and (D) 2000 sccm.
Figure 8:
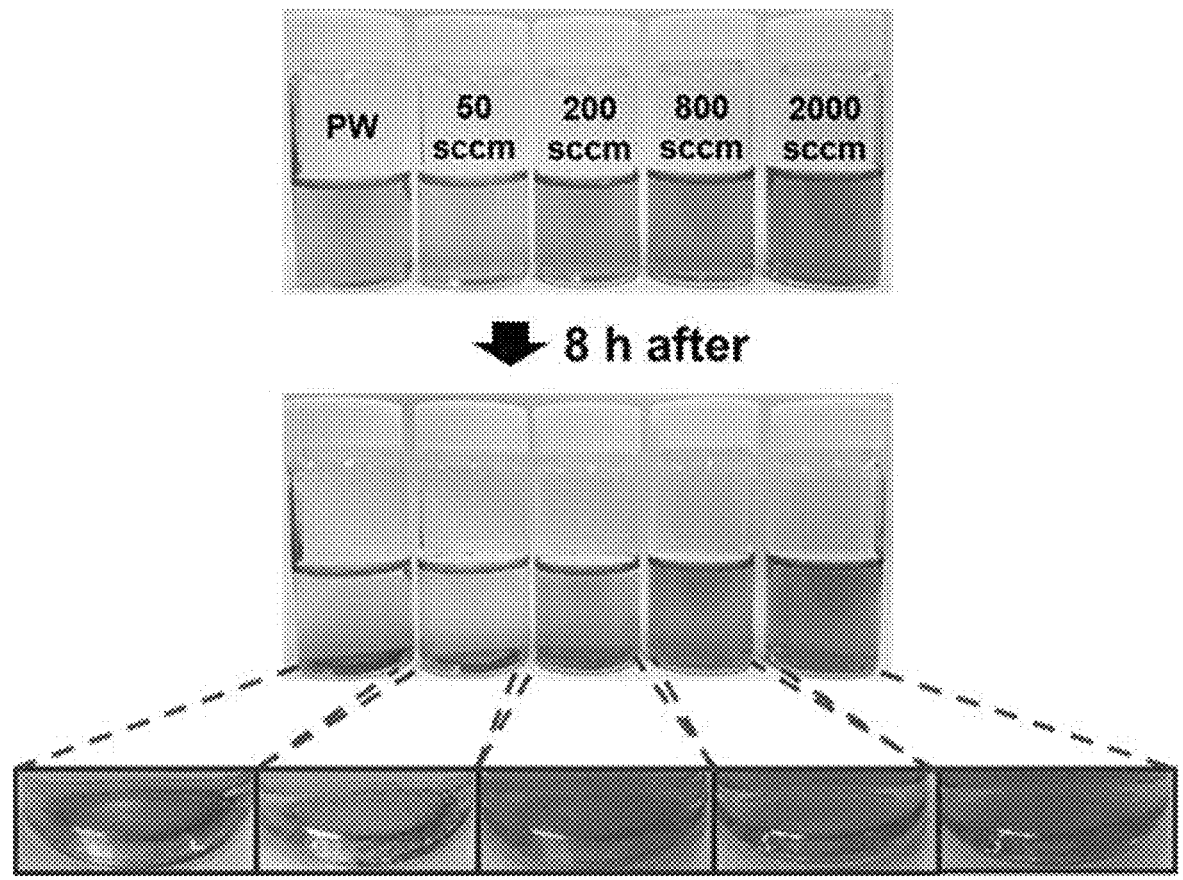
FIG. 8 shows images of CuPc crystals dispersed in water according to the carrier gas flow speed.
Figure 9:
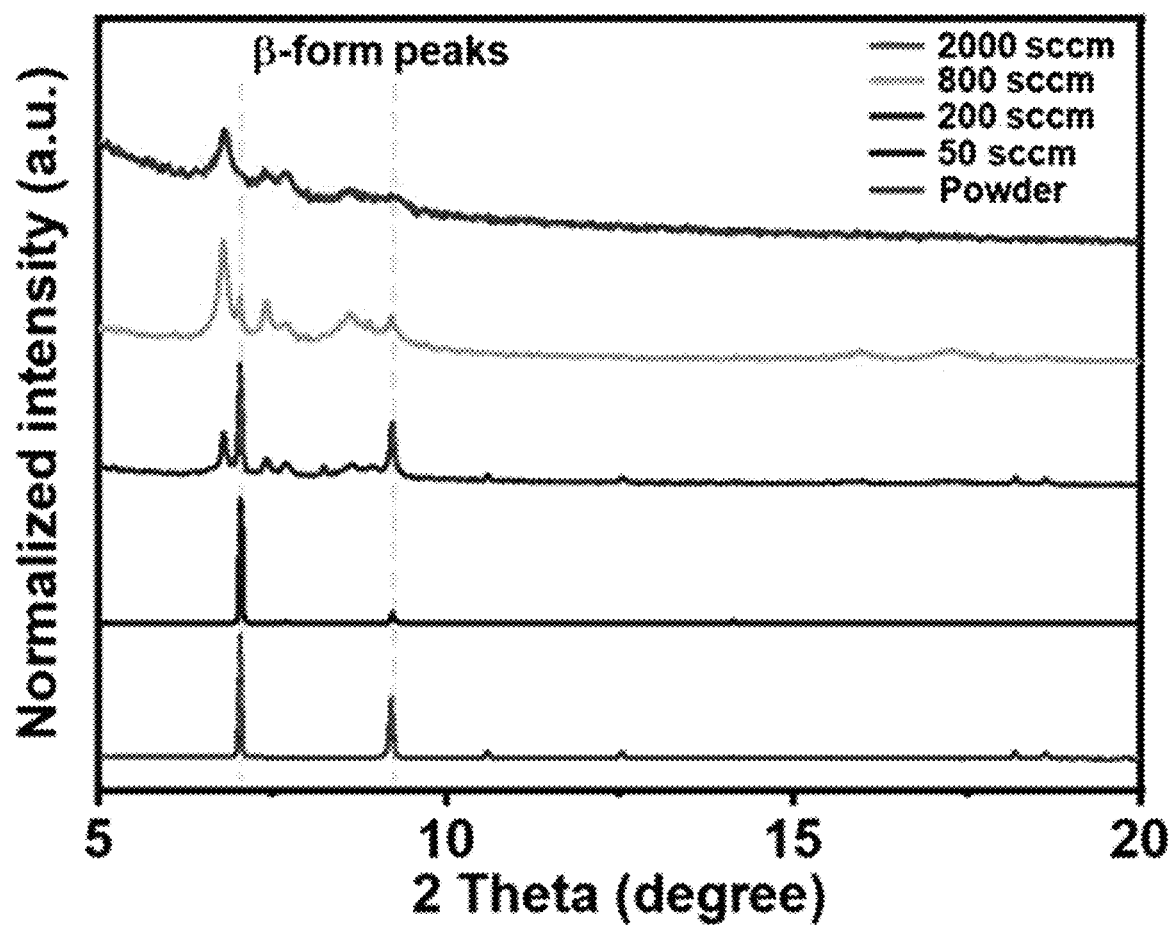
FIG. 9 shows the PXRD pattern of CuPc nanowire crystals grown at different flow speeds.

Example 4. Analysis of Characteristics of CuPc Nanowires According to Carrier Gas Flow Speed To investigate broader applications, phase control was attempted on copper phthalocyanine (CuPc), which is well-known as an excellent hole injection material for light-emitting diodes. Due to its low solubility in organic solvents, uniformly coating CuPc on a target substrate is a major limitation in device applications. Accordingly, the water dispersibility of CuPc was improved by reducing the size of CuPc crystals by controlling the flow speed of the carrier gas. Similar to ZnPc, CuPc exhibited a nanowire-like morphology and width of CuPc NWs, which were successfully reduced by increasing the flow speed of the carrier gas (FIG. 7). Through the water dispersibility test, it was identified that CuPc NWs grown in a high flow speed carrier gas had excellent water dispersibility. From the results of FIG. 8, the present inventor was convinced that the flow speed control method is applicable to various Pc crystals.

In summary, the present inventors successfully obtained a high yield of α-form ZnPc NWs exhibiting high water dispersibility, with negligible agglomeration or precipitation. By adjusting the carrier gas flow speed during PVT, the α-form ZnPc NWs can be selectively produced. Morphological observations and crystal structure analyses demonstrated that the width of ZnPc crystals could be controlled by the carrier gas flow speed, which in turn affected the ZnPc crystal phase. UV-VIS analysis of crystals grown at a flow speed of 2000 sccm showed that over 98% of the ZnPc produced was the α-form. These results demonstrate that flow speed control may be an effective method for obtaining ZnPc crystals of a desired phase.

The invention claimed is:

1. A method of preparing M-phthalocyanine nanowires, the method comprising:
   1) Vaporizing M-phthalocyanine, wherein M is zinc or copper;
   2) Transporting the vaporized M-phthalocyanine of step 1) using an inert gas at a flow speed of 1900 to 2100 sccm; and
   3) collecting the transported vaporized M-phthalocyanine of step 2) and precipitating the same in the form of M-phthalocyanine crystals.

2. The method of claim 1, wherein the M-phthalocyanine compound of step 1) is vaporized at a temperature of 470 to 700° C.

3. The method of claim 1, wherein the collection in step 3) is condensing and recrystallizing on a Si(100) substrate at a temperature from room temperature to 80° C.

4. The method of claim 1, further comprising sonification step after step 3).

5. The method of claim 1, wherein the prepared M-phthalocyanine nanowire has a diameter of 30 to 50 nm, and a length of 1 to 10 μm.

6. M-phthalocyanine nanowires prepared by the preparation method of claim 1.

7. The M-phthalocyanine nanowires of claim 6, wherein the M-phthalocyanine nanowires include 95 wt % or more of α-form crystals of Formula (3):

[Formula 3]

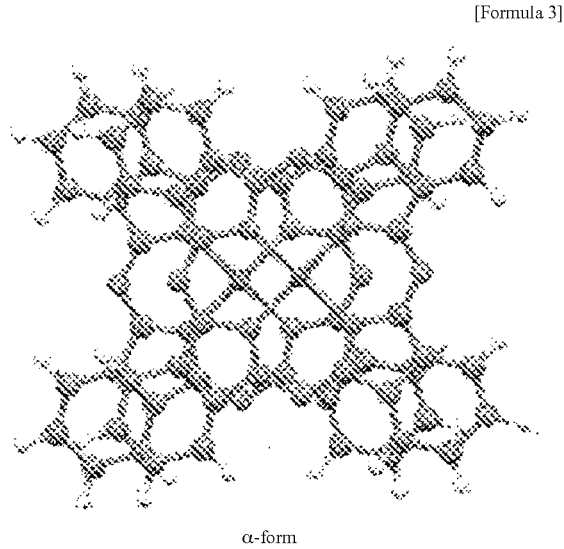

α-form

8. The M-phthalocyanine nanowires of claim 6, wherein the M-phthalocyanine nanowires include 98 wt % or more of α-form crystals of Formula (3):

[Formula 3]

α-form

* * * * *